United States Patent
Partyka et al.

[11] 3,980,667
[45] Sept. 14, 1976

[54] ANTI-ARRHYTHMIC 5-ENDO-SUBSTITUTED OXY-N-(AMINOLOWERALKYL)BICYCLE [2.2.2.]OCTANE-2,3-DI-ENDO-CARBOXYLIC ACID IMIDES

[75] Inventors: Richard Anthony Partyka; Henry Michael Holava, both of Liverpool, N.Y.; Alex Michael Jelenevsky, Greensboro, N.C.

[73] Assignee: Bristol-Myers Company, New York, N.Y.

[22] Filed: Mar. 5, 1975

[21] Appl. No.: 555,651

[52] U.S. Cl. .................... 260/326 C; 260/247.2 A; 260/268 TR; 260/293.61; 260/295 T; 260/295 ST; 260/343.3 R; 424/248; 424/250; 424/267; 424/274
[51] Int. Cl.² .................................. C07D 209/48
[58] Field of Search .............. 260/326 C, 247.2 A, 260/268 TR, 293.61

[56] References Cited
UNITED STATES PATENTS
3,850,922   11/1974   Matuo et al. .................... 260/326 C

*Primary Examiner*—Lewis Gotts
*Assistant Examiner*—S. P. Williams
*Attorney, Agent, or Firm*—Robert E. Havranek

[57] ABSTRACT

Series of 5-endo-benzoyloxy-N-[amino(lower)alkyl]bicyclo[2.2.2]octane-2,3-di-endo-carboxylic acid imides, 5-endo-(3-indolecarbonyloxy)-N-[amino(lower)alkyl]bicyclo[2.2.2]octane-2,3-di-endo-carboxylic acid imides, 5-endo-substituted-carbamoyloxy-N-[amino(lower)alkyl]bicyclo[2.2.2]octane-2,3-di-endo-carboxylic acid imides and 5-endo-(1-naphthoyloxy)-N-[amino(lower)alkyl]bicyclo[2.2.2]octane-2,3-di-endo-carboxylic acid imides have been found to possess unique prophylactic and therapeutic activity as anti-arrhythmia agents. An example of such a compound possessing activity is 5-endo-(3-indolecarbonyloxy)-N-(3-dimethylaminopropyl)bicyclo[2.2.2]octane-2,3-di-endo-carboxylic acid imide hydrochloride of the formula

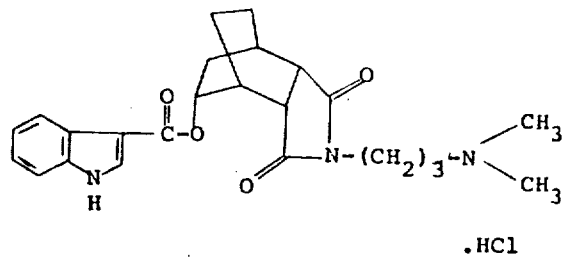

.HCl

6 Claims, No Drawings

ANTI-ARRHYTHMIC 5-ENDO-SUBSTITUTED OXY-N-(AMINOLOWERALKYL)BICYCLE [2.2.2.]OCTANE-2,3-DI-ENDO-CARBOXYLIC ACID IMIDES

BACKGROUND OF THE INVENTION

1. Field of the Invention

This invention relates to a novel series of 5-endo-benzoyloxy-, -substituted-carbamoyloxy-, (3-indolecarbonyloxy), or (1-naphthoyloxy)-N-[amino(lower)alkyl]bicyclo-[2.2.2]octane-2,3-di-endo-carboxylic acid imides possessing anti-arrhythmic and/or anti-fibrillatory activity.

2. Description of the Prior Art:

A. British Pat. No. 1,042,840 describes compounds having the formula in which each of R' and R'' represent hydrogen, or together an alkylene group having 1 or 2 carbon atoms, and R represents an alkyl group having 6 to 18, preferably 8 to 12 carbon atoms in a straight chain as having particularly advantageous properties as functional fluids.

B. U.S. Pat. No. 2,393,999 describes the compounds having the formula as being an effective insecticide.

C. U.S. Pat. No. 2,424,220 describes the compound having the formula as being an effective insecticide.

D. U.S. Pat. No. 2,462,835 describes the compound having the formula in which R is alkyl, alkene, aryl, substituted aryl, alkynyl, etc. as insecticides.

E. Culberson and Wilder, Jr., J. Org. Chem., 25, pp. 1358–62 (1960) report the preparation of compounds having the formula in which R is $CH_3$, $C_6H_{13}$ or hydrogen.

F. Rice, Reide and Grogan, J. Org. Chem., 19, pp. 884–893 (1954) report the preparation of compounds of the formula in which R is alkyl and their subsequent reduction with lithium aluminum hydride.

G. Worrall, J. Am. Chem. Soc., 82, pp. 5707–5711 (1960) reports the preparation of compounds having the formula H. German Auslegeschrift No. 1,179,205 reports the preparation of compounds having the formula

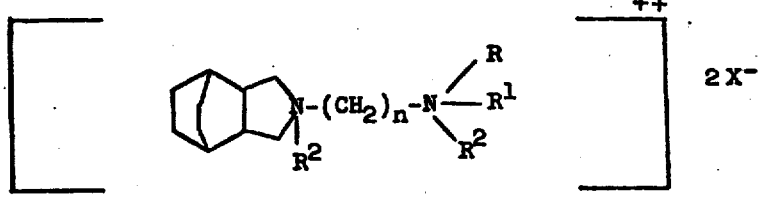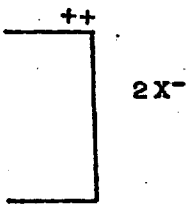

in which the bicyclo[2.2.2]octane ring system is saturated or unsaturated and/or substituted, R and $R^1$ are alkyl or alkenyl groups of 1 to 5 carbon atoms, or when combined with the nitrogen a heterocyclic ring. $R^2$ is a (lower)alkyl group, $n$ is a number of 2 to 5 and X a halogen anion. The quaternary compounds are described as having therapeutic properties in the treatment of cardiovascular disease, specifically high blood pressure.

I. U.S. Pat. No. 3,850,922 discloses and claims the compounds having the formula

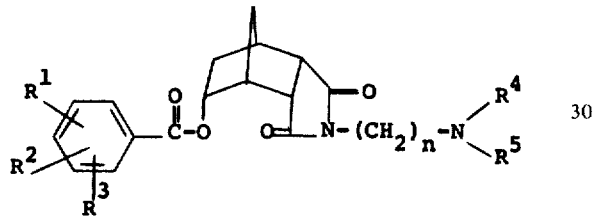

wherein $R^1$, $R^2$ or $R^3$ is H, Cl, Br, F, (lower)alkyl, nitro, OH or (lower)alkoxy, $n$ is an integer of 2 to 4 inclusive and $R^4$ or $R^5$ is H, (lower)alkyl or when taken together with the nitrogen a radical of the formula

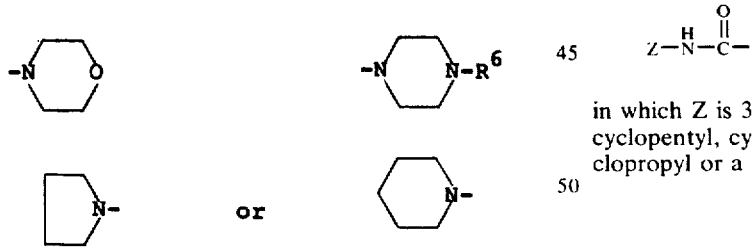

in which $R^6$ is (lower)alkyl; or a pharmaceutically acceptable acid addition salt thereof as anti-arrhythmic agents.

J. U.S. Pat. No. 3,850,921 discloses and claims the compounds having the formula

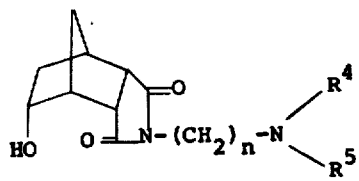

wherein $n$ is an integer of 2 to 4 inclusive and $R^4$ and $R^5$ are H, (lower)alkyl or when taken together with the nitrogen a radical of the formula

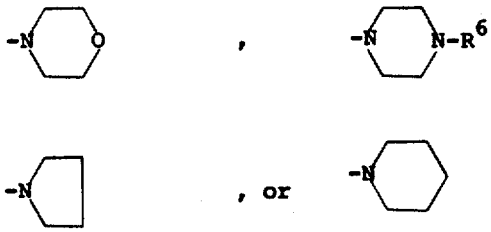

in which $R^6$ is (lower)alkyl; or an acid addition salt thereof as intermediates in the preparation of the anti-arrhythmia compounds found in U.S. Pat. No. 3,850,922 supra.

SUMMARY OF THE INVENTION

Compounds having the formula

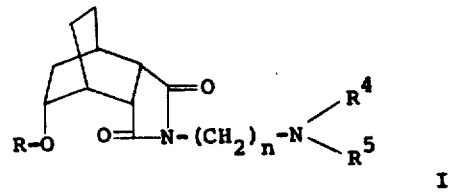

I wherein R is H or a radical having the formula $$Z-\overset{H}{N}-\overset{O}{\overset{\|}{C}}-$$

in which Z is 3 or 4-pyridyl, (lower)alkyl, cyclohexyl, cyclopentyl, cycloheptyl, 1-adamantyl, cyclobutyl, cyclopropyl or a radical of the formula

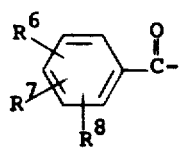

wherein $R^1$, $R^2$ and $R^3$ are alike or different and each is H, Cl, Br, F, (lower)alkyl, nitro, OH or (lower)alkoxy; or R is a radical having the formula wherein $R^6$, $R^7$ or $R^8$ is H, Cl, Br, F, (lower)alkyl, nitro, OH or (lower)alkoxy; or R is a radical having the formula

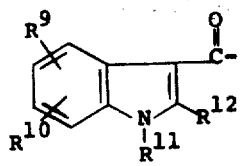

wherein $R^{11}$ is hydrogen or (lower)alkyl, $R^{12}$ is chloro, bromo, fluoro, hydrogen or (lower)alkyl and $R^9$ and $R^{10}$ are alike or different and each is H, Cl, Br, F, (lower)alkyl, nitro, $CF_3$, OH or (lower)alkoxy; or R is a radical having the formula

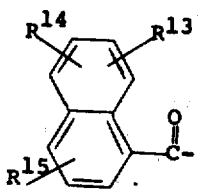

wherein $R^{13}$, $R^{14}$ and $R^{15}$ are alike or different and each is H, Cl, Br, F, (lower)alkyl, nitro, OH or (lower)alkoxy; n is an integer of 2 to 4 inclusive and $R^4$ and $R^5$ are alike or different and each is H, (lower)alkyl or when taken together with the nitrogen a radical of the formula

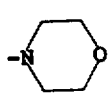 , 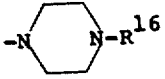 ,

 or 

in which $R^6$ is (lower)alkyl; or a pharmaceutically acceptable acid addition salt thereof are anti-arrhythmic agents.

Cardiac arrhythmia, a phenomenon commonly associated with coronary heart disease or myocardial infarction, is an affliction not uncommon in humans, especially the elderly. The mechanism of cardiac arrhythmia is suspected to be caused by an abnormal "focus" in the ventricle of the heart which sends out (fires) nerve signals more rapidly than required for the normal beating of the heart. Uncontrolled arrhythmia can lead to fibrillation which results in death.

It has been discovered that the series of compounds herein designated 5-endo-benzoyloxy-N-[amino-(lower)-alkyl]-bicyclo[2.2.2]octane-2,3-di-endo-carboxylic acid imides having the formula

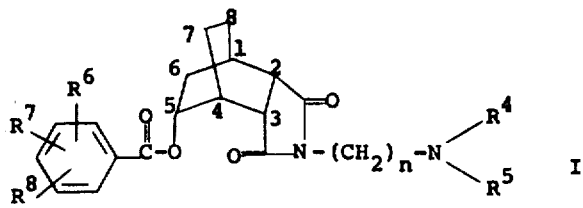 I wherein $R^6$, $R^7$ or $R^8$ are alike or different and each is H, Cl, Br, F, (lower)alkyl, nitro, OH or (lower)-alkoxy; or the compounds herein designated 5-endo-(1-naphthoyloxy)-N-[amino-(lower)alkyl]-bicyclo[2.2.2]octane-2,3-di-endo-carboxylic acid imides having the formula

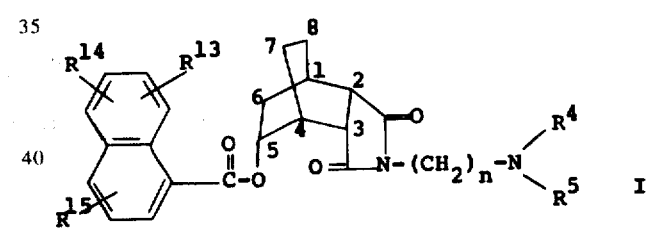 I wherein $R^{13}$, $R^{14}$ or $R^{15}$ are alike or different and each is H, Cl, Br, F, (lower)alkyl, nitro, OH or (lower)alkoxy; or the compounds herein designated 5-endo-(3-indolecarbonyloxy)-N-[amino-(lower)alkyl]-bicyclo[2.2.2]octane-2,3-di-endo-carboxylic acid imides having the formula

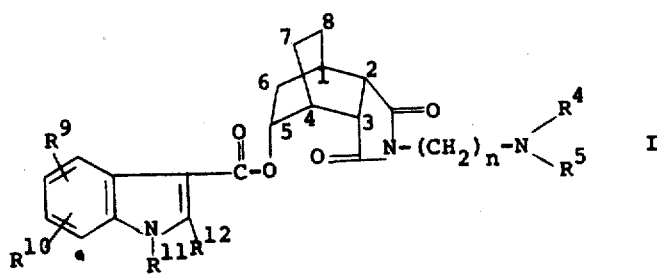 I wherein $R^{11}$ is hydrogen or (lower)alkyl, $R^{12}$ is Cl, Br, F, hydrogen or (lower)alkyl and $R^9$ and $R^{10}$ are alike or different and each is H, Cl, Br, F, (lower)alkyl, nitro, OH or (lower)alkoxy; or the compounds herein designated 5-endo-substituted-carbamoyloxy-N-[amino-(lower)alkyl]bicyclo[2.2.2-octane-2,3-di-endo-carboxylic acid imides having the formula

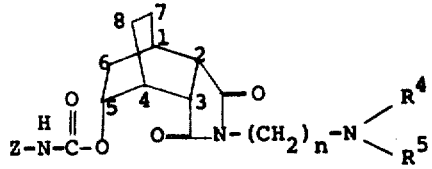

in which Z is (lower)alkyl, cyclohexyl, cyclopentyl, cyclobutyl, cycloheptyl, cyclopropyl or a radical of the formula

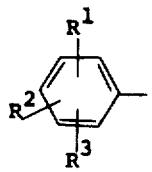

wherein $R^1$, $R^2$ and $R^3$ are alike or different and each is H, Cl, Br, F, (lower)alkyl, nitro, OH or (lower)-alkoxy; $n$ is an integer of 2 to 4 inclusive and $R^4$ and $R^5$ are alike or different and each is H, (lower)-alkyl or when taken together with the nitrogen a radical of the formula

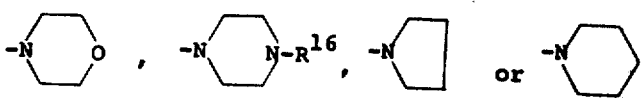

in which $R^{16}$ is (lower)alkyl; or a pharmaceutically acceptacle acid addition salt thereof are useful therapeutic or prophylactic agents in the suppression of the abnormal ectopic beat.

Compound I can theoretically exist in several isomeric forms, namely;
A. endo-R-oxy:endo-substituted imide;
B. exo-R-oxy:exo-substituted imide (X);
C. endo-R-oxy:exo-substituted imide; and
D. exo-R-oxy:endo-substituted imide.

Furthermore, each of these isomers has two optical isomers; levorotatory and dextrorotatory.

The distinction between the isomers is determined by the relative position of the constituent bonds at positions 2, 3 and 5 of the bicyclo ring system.

When these bonds, i.e., the constituent bonds at positions 2, 3 and 5 are on the same side as the $C_7-C_8$ bridge, we have the exo-exo isomer. When these bonds, i.e., the constituent bonds at positions 2, 3 and 5 are on the opposite side of the $C_7-C_8$ bridge or alternately within the cage formed by carbon atoms 2, 3, 5 and 6, then we have the endo-endo isomer. When the constituent bond at position 5 is on the same side as the $C_7-C_8$ bridge and the constituents bond 2 and 3 are on the opposite side of the $C_7-C_8$ bridge, then we have the exo(5-position)-endo(2,3-position)isomer. When the constituent bond at position 5 is on the opposite side of the $C_7-C_8$ bridge and the constituents bonds 2 and 3 on the same side as the $C_7-C_8$ bridge, we have the endo-exo isomer. Illustrative of the exo-exo isomer if the compound having the formula

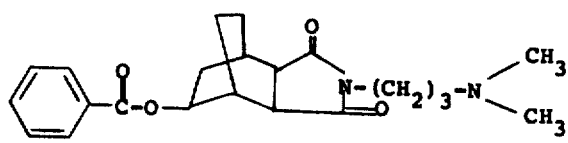

Illustrative of endo-endo is the compound of formula I.

The only isomers claimed in this invention are the endo-endo isomers as represented by compound I and the dextro- and levorotatory isomers thereof. The endo-endo isomers are inherently exclusively produced by the synthesis described herein.

Some exo-endo isomers have been prepared by another synthetic route as described in U.S. Pat. No. 3,850,922 and have found to be inactive in regulating cardiac arrhythmia, e.g., 5-exo-benzoyloxy-N-(3-dimethylaminopropyl)-bicyclo[2.2.1]heptane-2,3-di-endo-carboxylic acid imide hydrochloride.

The optical isomers can be separated and isolated by fractional crystallization of the diastereoisomeric salts formed, for instance, with (+) or (−)-tartaric acid or D-(−)-camphor sulfonic acid (see experimental).

For the purpose of this disclosure, the term "(lower)alkyl" is defined as an alkyl radical containing 1 to 6 carbon atoms. The term "(lower)alkoxy" is an alkoxy radical containing 1 to 6 carbon atoms. The term "pharmaceutically acceptacle acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of formula I with hydrochloric, sulfuric, nitric, phosphoric, phosphorous, hydrobromic, maleic, ascorbic, citric or tartaric, pamoic, lauric, stearic, palmitic, oleic, myristic, laurylsulfonic, napthalenesulfonic, linoleic or linolenic acid, and the like.

A preferred embodiment of the present invention is the compound having the formula

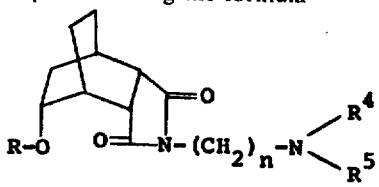

wherein R is H or a radical having the formula

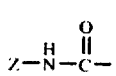

in which Z is 3 or 4-pyridyl, (lower)alkyl, cyclohexyl, cyclopentyl, cycloheptyl, 1-adamantyl, cyclobutyl, cyclopropyl or a radical of the formula

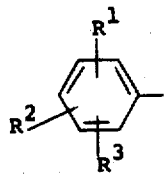

wherein $R^1$, $R^2$ and $R^3$ are alike or different and each is H, Cl, Br, F, (lower)alkyl, nitro, OH or (lower)alkoxy; or R is a radical having the formula

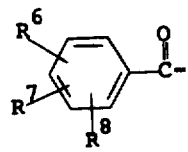

wherein $R^6$, $R^7$ or $R^8$ are alike or different and each is H, Cl, Br, F, (lower)alkyl, nitro, OH or (lower)alkoxy; or R is a radical having the formula

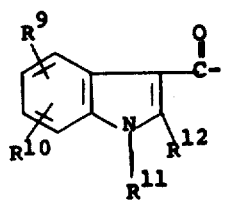

wherein $R^{11}$ is hydrogen or (lower)alkyl, $R^{12}$ is chloro, bromo, fluoro, hydrogen or (lower)alkyl and $R^9$ and $R^{10}$ are alike or different and each is H, Cl, Br, F, (lower)alkyl, nitro, $CF_3$, OH or (lower)alkoxy; or R is a radical having the formula

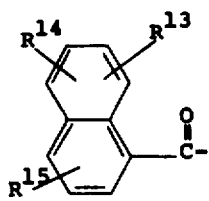

wherein $R^{13}$, $R^{14}$ and $R^{15}$ are alike or different and each is H, Cl, Br, F, (lower)alkoxy; n is an integer of 2 to 4 inclusive and $R^4$ or $R^5$ are alike or different and each is H, (lower)alkyl or when taken together with the nitrogen a radical of the formula

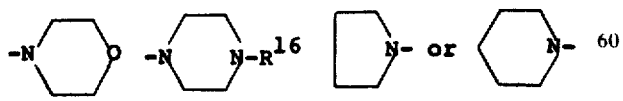

in which $R^{16}$ is (lower)alkyl; or a pharmaceutically acceptable acid addition salt thereof.

Another preferred embodiment of the present invention is the compound having the formula

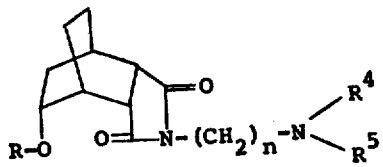

wherein R is H or a radical having the formula

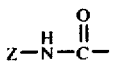

in which Z is a radical of the formula

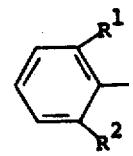

wherein $R^1$ and $R^2$ are alike or different and each is H, Cl, Br, F, (lower)alkyl, nitro, OH or (lower)alkoxy; or R is a radical having the formula

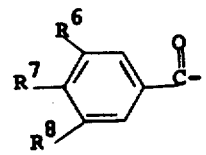

wherein $R^6$, $R^7$ or $R^8$ is alike or different and each is H, Cl, Br, F, (lower)alkyl, nitro, OH or (lower)alkoxy; or R is a radical having the formula

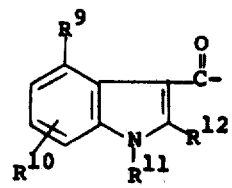

wherein $R^{11}$ is hydrogen or (lower)alkyl, $R^{12}$ is Cl, Br, F, hydrogen or (lower)alkyl and $R^9$ and $R^{10}$ are alike or different and each is H, F, Cl, OH, Br, $CF_3$, (lower)alkoxy, or (lower)alkyl; or R is a radical having the formula

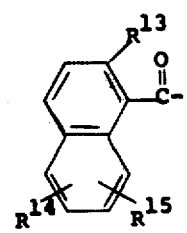

wherein $R^{13}$, $R^{14}$ and $R^{15}$ are alike or different and each is H, Cl, Br, F, (lower)alkyl, nitro, OH or (lower)alkoxy; n is an integer of 2 to 4 inclusive and $R^4$ and $R^5$ are alike or different and each is H, (lower)alkyl or when taken together with the nitrogen a radical of the formula

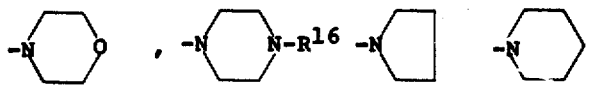

in which $R^{16}$ is (lower)alkyl; or a pharmaceutically acceptable acid addition salt thereof.

Another preferred embodiment of the present invention is the compound having the formula

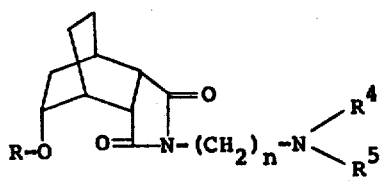

wherein R is H or a radical having the formula

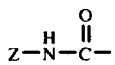

in which Z is a radical of the formula

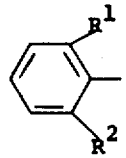

wherein $R^1$ and $R^2$ are alike or different and each is H, F, Cl, nitro or (lower)alkyl; or R is a radical having the formula

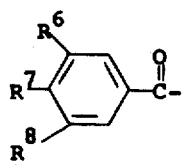

in which $R^6$, $R^7$ and $R^8$ are alike or different and each is H, F, Cl, nitro or (lower)alkoxy; or R is a radical having the formula

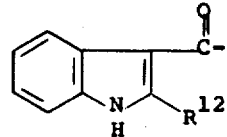

wherein $R^{12}$ is H, F, Cl, methoxy, ethoxy or n-propoxy; or R is a radical having the formula

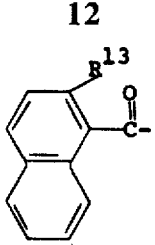

wherein $R^{13}$ is H, F, Cl, methoxy, ethoxy or n-propoxy, n is an integer of 2 to 4 inclusive and $R^4$ and $R^5$ are alike or different and each is H, (lower)alkyl or when taken together with the nitrogen a radical of the formula

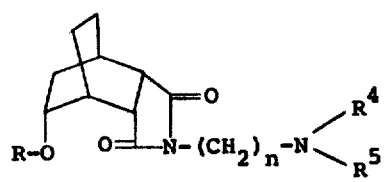

in which $R^{16}$ is (lower)alkyl; or a pharmaceutically acceptable acid addition salt thereof.

A most preferred embodiment of the present invention is the compound having the formula

wherein R is a radical having the formula

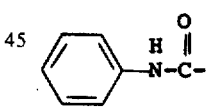 , 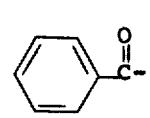

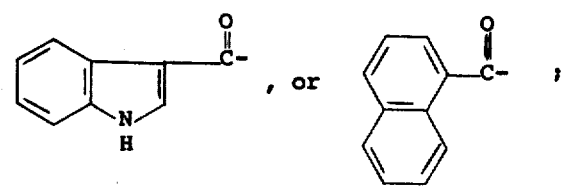

$R^4$ and $R^5$ are alike or different and each is (lower)alkyl; or a pharmaceutically acceptable acid addition salt thereof.

Another most preferred embodiment is the compound having the formula

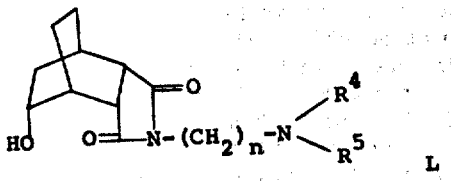

wherein $n$ is an integer of 2 to 4 inclusive and $R^4$ and $R^5$ are alike or different and each is H, (lower)alkyl or when taken together with the nitrogen a radical of the formula

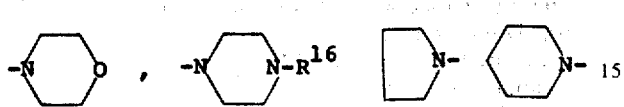

in which $R^{16}$ is (lower)alkyl; or an acid addition salt thereof.

Another most preferred embodiment is the compound L wherein $n$ is 3 and $R^4$ and $R^5$ are alike or different and each are (lower)alkyl; or an acid addition salt thereof.

Another most preferred embodiment is the compound L wherein $n$ is 3 and $R^4$ and $R^5$ are each methyl; or the hydrochloride salt thereof.

Especially preferred embodiments are the compounds having the formula I wherein
1. $n$ is 3, $R^4$ and $R^5$ are methyl and R is benzoyl;
2. $n$ is 3, $R^4$ and $R^5$ are methyl and R is phenylcarbamoyl;
3. $n$ is 3, $R^4$ and $R^5$ are methyl and R is 3-indolecarbonyl;
4. $n$ is 3, $R^4$ and $R^5$ are methyl and R is 1-naphthoyl; and
5. The hydrochloride salts of all the above compounds.
6. The essentially pure levorotatory isomers of the compound I.
7. The essentially pure dextrorotatory isomers of the compound I.

The objectives of the present invention have been achieved by the process of preparing the compounds having the formula

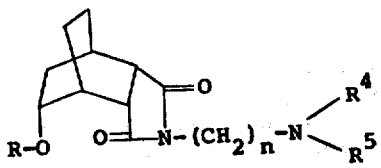

wherein R is a radical having the formula

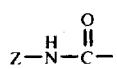

in which Z is 3 or 4-pyridyl, (lower)alkyl, cyclohexyl, cyclopentyl, cycloheptyl, 1-adamantyl, cyclobutyl, cyclopropyl or a radical of the formula

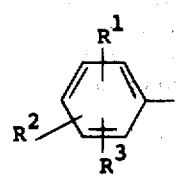

wherein $R^1$, $R^2$ and $R^3$ are alike or different and each is H, Cl, Br, F, (lower)alkyl, nitro, OH of (lower)alkoxy; or R is a radical having the formula

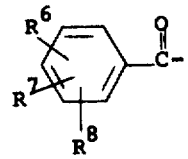

wherein $R^6$, $R^7$ or $R^8$ are alike or different and each is H, Cl, Br, F, (lower)alkyl, nitro, OH or (lower)alkoxy; or R is a radical having the formula

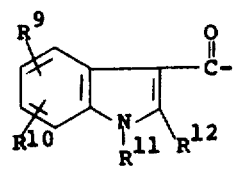

wherein $R^{11}$ is hydrogen or (lower)alkyl, $R^{12}$ is chloro, bromo, fluoro, hydrogen or (lower)alkyl and $R^9$ and $R^{10}$ are alike or different and each is H, Cl, Br, F, (lower)alkyl, nitro, $CF_3$, OH or (lower)alkoxy; or R is a radical having the formula

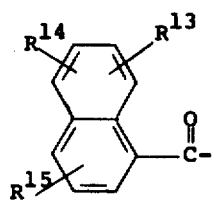

wherein $R^{13}$, $R^{14}$ and $R^{15}$ are alike or different and each is H, Cl, Br, F, (lower)alkyl, nitro, OH or (lower)alkoxy; $n$ is an integer of 2 to 4 inclusive and $R^4$ and $R^5$ are alike or different and each is H, (lower)alkyl or when taken together with the nitrogen a radical of the formula

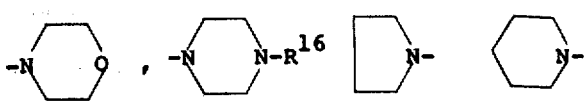

in which $R^{16}$ is (lower)alkyl; which process is characterized by the step consisting of treating one mole of the compound having the formula

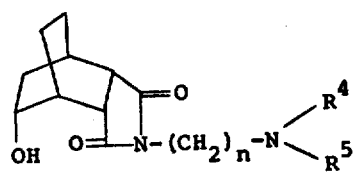

III in which $n$, $R^4$ and $R^5$ are as above with at least one mole of the compounds having the formula

in which Z is as defined above; or

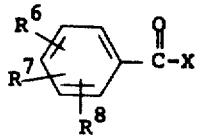

in which $R^6$, $R^7$ and $R^8$ are as defined above and X is chloro, bromo or iodo; or its chemical equivalent as an acylating agent, or

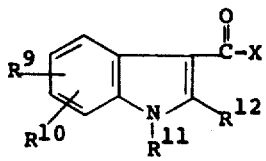

in which $R^9$, $R^{10}$, $R^{11}$ and $R^{12}$ are as defined above and X is chloro, bromo or iodo, or its chemical equivalent as an acylating agent, or

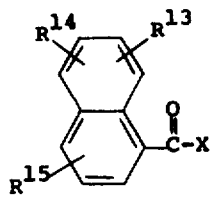

in which $R^{13}$, $R^{14}$ and $R^{15}$ are as defined above and X is chloro, bromo or iodo, or its chemical equivalent as an acylating agent, to produce compound I.

Another preferred embodiment is the process for the preparation of compounds of formula I which process is characterized by the step of treating one mole of the compound having the formula III in which $n$ is 3 and $R^4$ and $R^5$ are alike or different and each is H or (lower)alkyl with at least one mole of the compounds 8, 9, 10 or 11 in a reaction inert organic solvent, with or without the aid of heat, to produce compound I.

A most preferred embodiment is the process for producing compound I wherein compound 8 is phenyl isocyanate, compound 9 is benzoyl chloride, compound 10 is 3-indolecarbonyl chloride and compound 11 is 1-naphthoyl chloride.

For the purpose of this invention, the term "chemical equivalent as an acylating agent" is meant to include all those agents commonly known in the art to be useful for the esterification of alcohols, for example, acid anhydrides, mixed acid anhydrides, acid halides, and the like.

The compounds were tested in dogs for their reversion activity in ouabain-induced arrhythmia.

Anesthetized dogs were used for the production of ouabain-induced ventricular arrhythmias. The arrhythmia consisted of a nodal or ventricular tachycardia. The procedure used to establish the arrhythmia as well as the criteria employed to determine anti-arrhythmic activity generally was that employed by Lucchesi et al.[1]

The anti-arrhythmic activity of dl-5-endo-(3-indolecarbonyloxy)-N-(3-dimethylaminopropyl)-bicyclo[2.2.2]octane-2,3-di-endo-carboxylic acid imide hydrochloride (BL-4840A), dl-5-endo-(benzoyloxy)-N-(3-dimethylaminopropyl)-bicyclo[2.2.2]octane-2,3-di-endo-carboxylic acid imide hydrochloride (BL-3995A), dl-5-endo-phenylcarbamoyloxy-N-(3-dimethylaminopropyl)-bicyclo[2.2.2]octane-2,3-di-endo-carboxylic acid imide hydrochloride (BL-4649A) and 5-endo-(1-naphthoyloxy)-N-(3-dimethylaminopropyl)-bicyclo[2.2.2]octane-2,3-di-endo-carboxylic acid imide hydrochloride (BL-4710A) was determined by rapid intravenous injection and compared to lidocaine, disopyramide and aprindine. The average prolonged reversion doses are shown below:

| Compound | I. V. Reverting Dose, mg/kg* |
|---|---|
| BL-3995A | 1.0 (N=5) |
| BL-4649A | 0.77 ± 0.23 (N=3) |
| BL-4710A | 1.2 ± 0.37 (N=6) |
| BL-4840A | 1.0 (N=3) |
| Lidocaine | 6.4 ± 1.4 (N=8) |
| Disopyramide | 4.5 ± 1.3 (N=6) |
| Aprindine | 2.46 ± 0.83 (N=5) |

*Values are mean ± standard error; N = No. of animals.

EXAMPLES OF THE PREFERRED EMBODIMENTS

All temperatures are expressed in degrees centigrade.

EXAMPLE 1

5-endo-Hydroxy-N-(3-dimethylaminopropyl)-endo-cis-bicyclo[2.2.2]octane-2,3-di-endo-carboxylic acid imide (IIIa).

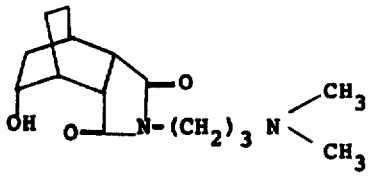

A mixture of the lactone-acid, bicyclo[2.2.2]-octane-endo-2,3-dicarboxylic acid-5-endo-hydroxy-γ-lactone (II) (1.96g., 0.01 mole) prepared according to the procedure of Chiu and Wright, [Can. J. Chem. 37, 1425 (1959)], 10 ml. thionyl chloride and 40 ml. $CH_2Cl_2$ was refluxed at 90° C. for 3 hours. Removal of the volatiles afforded the crystalline acid chloride (IIa) which was redissolved in 35 ml $CH_2Cl_2$. This solution was added slowly and with vigorous stirring to a solution of 3-dimethylaminopropylamine (1.53 g, 0.015 m) in 15 ml $CH_2Cl_2$. The initial reaction was exothermic. After refluxing for 19 hours and cooling, there was added 50 ml of saturated aqueous $NaHCO_3$. Extraction with $CH_2Cl_2$ followed. The extracts were washed with brine, dried ($Na_2SO_4$), filtered and stripped thereby affording crystalline hydroxy-imide 3. Recrystallization from ethyl acetate - Skelly B (essentially n-hexane) afforded a 48% yield of material, mp 108°-109°C.

Anal. calc'd. for $C_{15}H_{24}N_2O_3$: C, 64.26; H, 8.63; N, 9.99. Found: C, 63.87; H, 8.72; N, 9.65.

EXAMPLE 2

General Method of Preparation of 5-endo-Hydroxy-N-[amino(lower)alkyl]bicyclo[2.2.2]octane-2,3-di-endo-carboxylic Acid Imides (III).

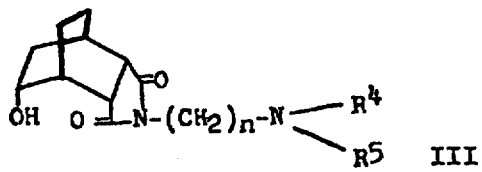

A mixture of 0.1 mole of lactone (II) from example 1 and 50 ml. of thionyl chloride was refluxed on a water bath for 2 hours. The excess thionyl chloride was removed in vacuo and an oily residue (IIa) remained that was washed with n-hexane (or petroleum ether). The oily residue was dissolved in 50 ml. of anhydrous benzene. To this solution was added a solution of 0.12 moles of the appropriate amine, e.g., N,N-dimethylaminopropylamine, and 100 ml. of anhydrous benzene with stirring. The mixture was then refluxed for about five hours and concentrated in vacuo. The resultant brown syrupy substance (IIb) was refluxed for five hours in 300 ml of of 50% water-ethanol containing 0.12 mole of potassium hydroxide ethanol. The solvents were removed in vacuo, saturated potassium carbonate solution added and the resultant solution extracted repeatedly using chloroform or 1:1 ethyl acetate-benzene. The collective organic extracts were washed with saturated sodium chloride solution and dried over anhydrous sodium sulfate. After filtration, the solution was concentrated in vacuo and the product was recovered by crystallization, chromatography and-/or vacuum distillation wherein in formula III, n 8c is an integer of 2 to 4 inclusive, $R^4$ or $R^5$ is H, (lower)alkyl or when taken together with the nitrogen a radical of the formula

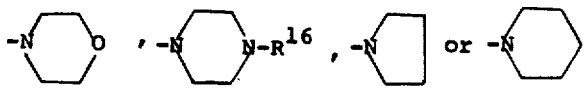

in which $R^{16}$ is (lower)alkyl.

EXAMPLE 3

5-endo-Benzoyloxy-N-(3-dimethylaminopropyl)-bicyclo[2.2.2]octane-2,3-di-endo-carboxylic acid imide hydrochloride (Ia).

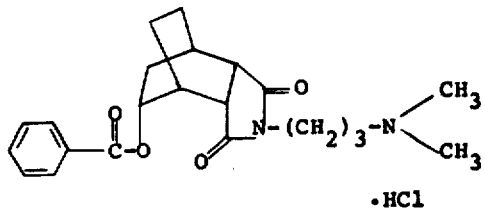

To a solution of hydroxy-imide 3 (2.8 g, 0.01 m) in 30 ml of pyridine was added benzoyl chloride (2.11 g, 0.015 m) and the resulting reaction mixture refluxed at 110° C. for 1 hour. The pyridine was removed under reduced pressure and there was added aqueous 5% $K_2CO_3$ to the residue. Extraction with ethyl acetate followed. The combined extracts were washed with brine, dried ($Na_2SO_4$), filtered and stripped. The residue so obtained was dissolved in ether and the hydrochloride salt prepared in the usual way after filtration from some insoluble materials. The hydrochloride salt was recrystallized from EtOH-Et$_2$O. This procedure afforded a 58% yield of ester-imide Ia; mp 217°–219° C. Recrystallization from $CH_3OH$-Et$_2$O and allowing the resulting dried crystals to equilibrate with atmospheric moisture afforded product with mp 217°–218°C.

Anal. calc'd. for $C_{22}H_{28}N_2O_4$.HCl: C, 62.92; H, 6.96; N, 6.72. Found: C, 56.19; H, 6.57; N, 6.02; KF-water 10.86. Correction for moisture: C, 62.81; H, 4.81; N, 6.73.

EXAMPLE 4

5-endo-N-phenylcarbamoyl-N-(3-dimethylaminopropyl)-bicyclo[2.2.2]octane-2,3-di-endo-carboxylic acid imide hydrochloride. (Ib).

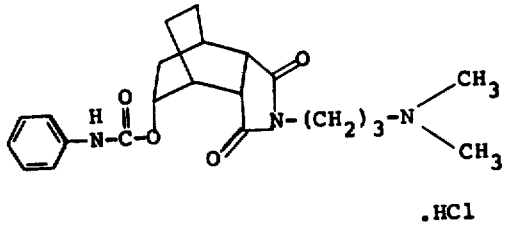

To a solution of the hydroxy-imide IIIa (1.4 g, 0.005 mole) in dry $CH_2Cl_2$ (30 ml) was added a solution of phenylisocyanate (1.19 g, 0.01 mole) in dry $CH_2Cl_2$ (15 ml). The mixture was stirred under anhydrous conditions at 25° C. for 19 hrs., whereupon the $CH_2Cl_2$ was removed under reduced pressure. The resultant crude foam was recrystallized from hot ethyl acetate (30 ml) to yield a solid which was then dissolved in 100% ethanol (25 ml). After adding HCl gas to the resulting solution, the solvent was removed under reduced pressure and the crude solid was recrystallized from isopropyl alcohol-methanol (30 ml:30 ml). In this manner, there was obtained 1.85 g. (94%) of the desired product after drying vacuum over $P_2O_5$; mp 249°–250° C.

Anal. calc'd. for $C_{22}H_{29}N_3O_4$.HCl: C, 60.61; H, 6.93; N, 9.64; Cl, 8.13. Found: C, 60.66; H, 6.96; N, 9.82; Cl, 8.01.

EXAMPLE 5

5-endo-(α-Naphthoyloxy)-N-(3-dimethylaminopropyl)-bicyclo[2.2.2]octane-2,3-di-endo-carboxylic acid imide hydrochloride (Ic).

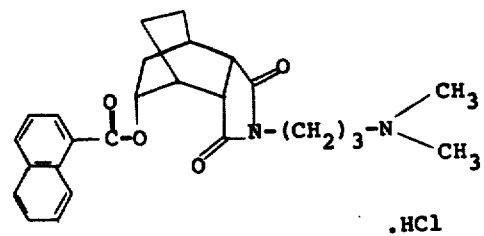

To a solution of the hydroxy-imide IIIa (1.76 g, 0.008 mole) in dry pyridine (35 ml) was added a solution of α-naphthoyl chloride [(3.80 g, 0.02 mole) prepared in the standard manner from α-naphthoic acid and thionyl chloride in dry pyridine (20 ml)]. The mixture was stirred under anhydrous conditions at 25°C. for 67 hours, whereupon the pyridine was removed under reduced pressure. The residue was then dissolved in 100% ethanol (75 ml), HCl gas was bubbled in and the solvent was stripped off under reduced pressure. The resultant amide oily-solid was recrystallized from 100% ethanol, affording 1.62 g (43%) of the desired product after drying under high vacuum and over $P_2O_5$; mp 186°–187°C.

Anal. calc'd. for $C_{26}H_{30}N_2O_4 \cdot HCl$: C, 66.30; H, 6.63; N, 5.95; Cl, 7.53. Found: C, 65.94; H, 6.69; N, 6.22; Cl, 7.71.

EXAMPLE 6

5-endo-(Indole-3-carbonyloxy)-N-(3-dimethylaminopropyl)-bicyclo[2.2.2]octane-2,3-di-endo carboxylic acid imide hydrochloride (Id).

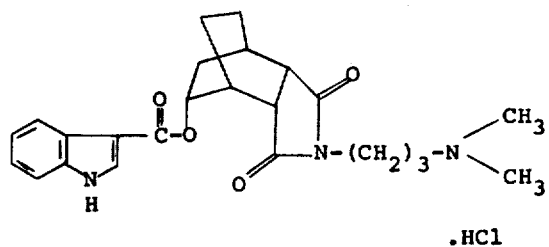

Indole-3-carboxylic acid (2.0 g, 0.0124 mole) was suspended in anhydrous $Et_2O$ (50 ml) and thionyl chloride (2.2 ml. excess) was added with stirring, followed by two drops of dry DMF (dimethylformamide), the mixture was stirred at 20° C. for 2 hrs., during which time complete solution was obtained. The solvent and excess reagent were stripped off under reduced pressure. The remaining solid acid chloride was dissolved in dry $CH_2Cl_2$ (70 ml) and alcohol IIIa (2.33g, 0.0083 mole) was added with stirring, followed by the addition of 1 ml of dry pyridine. The solution was then heated to reflux under anhydrous conditions. After 20 mins., a solid separated out, and heating was discontinued. The cooled slurry was filtered and the solid was recrystallized from absolute EtOH, affording white needles of pure product after drying under high vacuum over $P_2O_5$ at 78°. (3.14 g, 82%, mp 249°–253°).

Anal. calc'd. for $C_{24}H_{29}N_3O_4 \cdot HCl$: C, 62.67; H, 6.57; N, 9.14. Found: C, 62.39; H, 6.44; N, 9.29.

EXAMPLE 7

General Method of Preparation of 5-endo-(1-naphthoyloxy)-N-[amine(lower)alkyl]bicyclo[2.2.2]octane-2,3-di-endo-carboxylic Acid Imides (I).

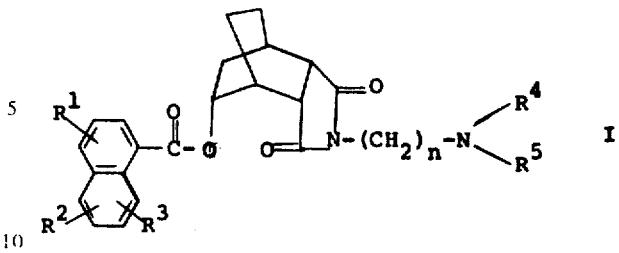

The 5-endo-Hydroxy-N-[amino(lower)alkyl]bicyclo-[2.2.2]octane-2,3-di-endo-carboxylic acid imide (III) (0.01 mole) obtained in example 2 was added to 50 ml. of a 100:1 pyridine-piperidine solution of 0.012 mole of an appropriate α-naphthoyl halide, e.g., 1-naphthoic acid chloride, with stirring. The resultant mixture was allowed to stand overnight in a refrigerator or warmed in a water or oil bath. The mixture was poured into ice-water and saturated with sodium carbonate and then extracted with chloroform or 1:1 benzene-ethyl acetate. The combined organic extracts were washed with saturated sodium chloride solution and dried over anhydrous sodium sulfate. The solution was collected by filtration and concentrated in vacuo to yield the desired title product (I).

EXAMPLE 8

General Method of Preparation of 5-endo-substituted-carbamoyloxy-N-[amino(lower)alkyl]bicyclo[2.2.2]-octane-2,3-di-endo-carboxylic Acid Imides (I).

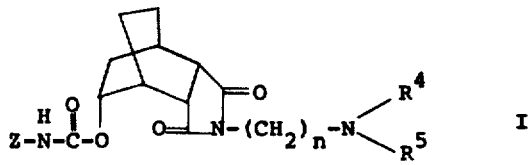

The 5-endo-Hydroxy-N-[amino(lower)alkyl]-bicyclo[2.2.2]octane-2,3-di-endo-carboxylic acid imide (III) (0.01 mole) obtained in example 2 is added to 50 ml. of pyridine solution of 0.012 mole of an appropriate isocyanate, e.g., phenyl isocyanate, with stirring. The resultant is refluxed for about 4 hours. The pyridine is removed in vacuo with the aid of added toluene. The resultant oil is dissolved in ethyl acetate, washed with water and brine, dried over anhydroux sodium sulfate, filtered, and the solvent removed to give an oil. Addition of $Et_2O$-Skellysolve B (essentially n-hexane) gives the free amine as a white solid which recrystallizes from an appropriate solvent. The amine is slurried in 20 ml EtOH and HCl gas is bubbled in to give a solution. The addition of $Et_2O$ produces a precipitate which is the monohydrochloride salt of the desired product.

EXAMPLE 9

Alternate Method of Preparation of 5-endo-Hydroxy-N-[amino(lower)alkyl]bicyclo[2.2.-2]octane-2,3-di-endo-carboxylic Acid Imides (III).

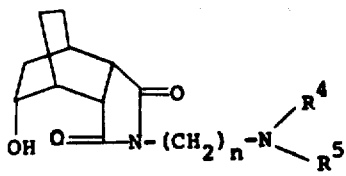

III

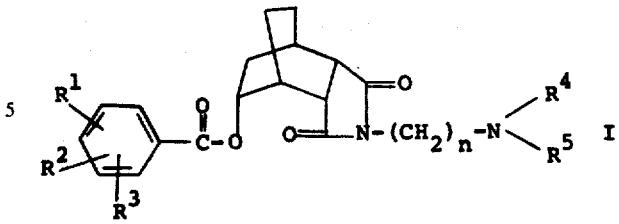

A mixture of 0.1 mole of acid-lactone (II) and 30 ml. of PCl₃ was refluxed in a water bath for two hours. The excess PCl₃ was removed in vacuo and washed with n-hexane. The oily residue was dissolved in 50 ml. of chloroform or methylene chloride and a solution of 0.12 mole of an appropriate amine, e.g., N, N-dimethylaminopropylamine, dissolved in 100 ml. of anhydrous chloroform or methylene chloride was added with stirring and cooling. Stirring was continued for 2 hours, following which mixture was warmed to room temperature following which the mixture was refluxed for about 15 minutes. The solution was washed with saturated potassium carbonate solution after cooling, separated, and the organic phase washed with saturated sodium chloride solution. The organic solution was dried over anhydrous sodium sulfate, filtered, and concentrated in vacuo. The material subsequently collected was the title product of formula III wherein n is an integer of 2 to 4 inclusive, $R^4$ or $R^5$ is H, (lower)alkyl or when taken together with the nitrogen a radical of the formula

,

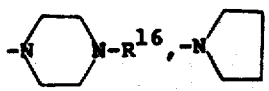

or 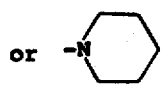

in which $R^{16}$ is (lower)alkyl.

EXAMPLE 10

General Method of Preparation of 5-endo-benzoyloxy-N-[amino(lower)alkyl]bicyclo[2.2.2]octane-2,3-di-endo-carboxylic Acid Imides (I).

The 5-endo-Hydroxy-N-[amino(lower)alkyl]-bicyclo[2.2.2]octane-2,3-di-endo-carboxylic acid imide (III) (0.01 mole) obtained in example 2 was added to 50 ml. of a 100:1 pyridine-piperidine solution of 0.012 mole of an appropriate benzoyl halide, e.g., benzoyl chloride, with stirring. The resultant mixture was allowed to stand overnight in a refrigerator or warmed in a water or oil bath. The mixture was poured into ice-water and saturated with sodium carbonate and then extracted with chloroform or 1:1 benzene-ethyl acetate. The combined organic extracts were washed with saturated sodium sulfate. The solution was collected by filtration and concentrated in vacuo to yield the desired title product (I).

EXAMPLE 11

General Method of Preparation of 5-endo-(3-indolecarbonyloxy)-N-[amino(lower)alkyl]bicyclo[2.2.2]octane-2,3-di-endo-carboxylic Acid Imides (I).

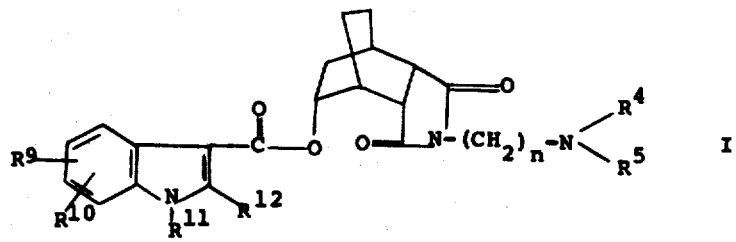

5-endo-Hydroxy-N[amino(lower)alkyl]-bicyclo[2.2.2]octane-2,3-di-endo-carboxylic acid imide (III) (0.01 mole) was added to a dry solution of appropriately substituted indole-3-carbonyl halide (0.011 mole), e.g., indole-3-carbonyl chloride, in methylene chloride containing approximately 1 ml. of pyridine, with stirring. The resultant mixture was allowed to stand overnight in a refrigerator or warmed in a water or oil bath. The mixture was poured into ice-water and saturated with sodium carbonate and then extracted with chloroform or 1:1 benzene-ethyl acetate. The combined organic extracts were washed with saturated sodium chloride solution and dried over anhydrous sodium sulfate. The solution was collected by filtration and concentrated in vacuo to yield the desired title product (I).

EXAMPLE 12

5-endo-Hydroxy-N-(2-dimethylaminoethyl)bicyclo[2.2.2]octane-2,3-di-endo-carboxylic Acid Imide (IIIb).

Substitution in the procedure of example 1, 2 or 9 for the "appropriate" amine used therein of an equimolar quantity of N,N-dimethylaminoethylamine produces the title product.

EXAMPLE 13

5-endo-Hydroxy-N-(2-diethylaminoethyl)bicyclo[2.2.2]-octane-2,3-di-endo-carboxylic Acid Imide (IIIc).

Substitution in the procedure of example 2 for the "appropriate" amine used therein of an equivalent amount of N,N-diethylaminoethylamine produces the title product.

EXAMPLE 14

5-endo-Hydroxy-N-(3-diethylaminopropyl)bicyclo-[2.2.2]octane-2,3-di-endo-carboxylic Acid Imide (IIId).

Substitution in the procedure of example 2 for the "appropriate" amine used therein of an equivalent amount of N,N-diethylaminopropylamine produces the title product.

EXAMPLE 15

5-endo-Hydroxy-N-(3-piperidinopropyl)bicyclo-[2.2.2]octane-2,3-di-endo-carboxylic Acid Imide (IIIe).

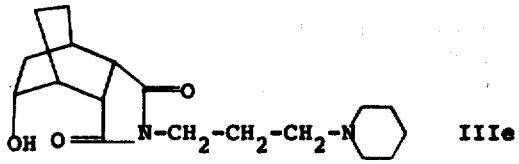

IIIe

Substitution in the procedure of examples 2 or 9 for the "appropriate" amine used therein of an equivalent amount of 3-piperidinopropylamine produces the title product.

EXAMPLE 16

5-endo-Hydroxy-N-(2-morpholinoethyl)bicyclo-[2.2.2]octane-2,3-di-endo-carboxylic Acid Imide Hydrochloride (IIIf).

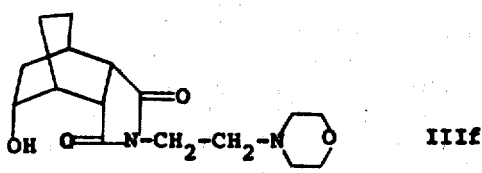

IIIf

Substitution in the procedure of examples 2 or 9 for the "appropriate" amine used therein of an equivalent amount of morpholinoethylamine produces the title compound which is collected as the hydrochloride. The hydrochloride salt is prepared by dissolving IIIf in a minimal amount of diethylether followed by the addition of a solution of dry HCl gas to the solution of IIIf with stirring and scratching. The resultant precipitate is collected by filtration and is determined to be the hydrochloride of the desired title product.

EXAMPLE 17

5-endo-Hydroxy-N-(3-morpholinopropyl)bicyclo[2.2.2]-octane-2,3-di-endo-carboxylic Acid Imide (IIIg).

Substitution in the procedure of example 2 for the "appropriate" amine used therein of an equivalent amount of morpholinopropylamine produces the title product.

EXAMPLE 18

Resolution of (+)-5-endo-Benzoyloxy-N-(3-dimethylaminopropyl)-bicyclo[2.2.2.]octane-2,3-di-endo-carboxylic Acid Imide Hydrochloride (Ia).

I. Preparation of the (−)-enantiomer.

A. (+)-5-endo-Benzoyloxy-N-(3-dimethylaminopropyl)bicyclo[2.2.2]octane-2,3-di-endo-carboxylic Acid Imide (Ia).

A stirred mixture of the hydrochloride salt of Ia (10 g.) in water (150 ml.) and ether (200 ml.) is neutralized by the addition of sodium carbonate. The aqueous layer is re-extracted with ether (2 × 200 ml.). The combined ethereal extracts are washed with water, followed by water saturated with sodium chloride (3×) and dried (sodium sulfate). Removal of the ether leaves colorless crystals of the racemic base Ia.

B. (+)-10-Camphorsulfonic Acid Salt of (−)-5-endo-benzoyloxy-N-(3-dimethylaminopropyl)-bicyclo[2.2.2]octane-2,3-di-endo-carboxylic Acid Imide.

A hot solution of (+)-10-camphorsulfonic acid (276.5 g., 1.19 mole) in ethanol (1.1.1) is added to a hot solution of the racemic base Ia (441.1 g., 1.19 mole) in ethanol (3.5.1) containing water (175 ml.). The solution is heated to near boiling and then rapidly cooled to 20°. The colorless crystalline material which forms during 3 hours standing at 20° is collected and washed with cold ethanol (600 ml.) to give the title product. The salt is recrystallized from acetonitrile to give colorless needles. The ethanolic mother liquor is retained for isolation of the (+)-isomer.

C. (−)-5-endo-Benzoyloxy-N-(3-dimethylaminopropyl)bicyclo[2.2.2]octane-2,3-diendo-carboxylic Acid Imide [(−)-Ia].

The camphorsulfonic acid salt from step B is partitioned between a stirred mixture of ethyl acetate (3.5.1) and water (3.1) containing sodium carbonate (150 g.). The aqueous layer is re-extracted with ethyl acetate (600 ml.). The combined ethyl acetate extracts are washed with water saturated with sodium chloride (3x), and dried (sodium sulfate). Removal of the ethyl acetate leaves the title product as colorless crystals.

D. (−)-5-endo-Benzoyloxy-N-(3-dimethylaminopropyl)bicyclo[2.2.2]octane-2,3-diendo-carboxylic Acid Imide Hydrochloride (V).

To a near boiling solution of the (−)-isomer from step C in 95% ethanol (3.5l) is added 475 ml. of 95% ethanol, 0.988 molar in hydrogen chloride (0.468 mole of HCl). The solution is cooled in ice. The colorless crystals are collected, washed with cold 95% ethanol (600 ml.) and dried to give the title product.

II. Preparation of the (+)-enantiomer.

A. (−)-Tartaric Acid Salt of (+)-5-endo-benzoyloxy-N-(3-dimethylaminopropyl)-bicyclo[2.2.2]octane-2,3-di-endo-carboxylic Acid Imide.

The ethanolic mother liquor from step I B. above is stored at 0° for 90 hours to give additional crystalline material. The filtrate is concentrated to give another crop of colorless crystals. Both crops are combined and partitioned between ethyl acetate and aqueous sodium carbonate as described in 1 C. above to give a mixture of (+)- and (−)-isomers greatly enriched in the (+)-enantiomer.

(—)-Tartaric acid (89.6 g., 0.596 mole) is added to a hot stirred solution of the (+)-enriched mixture in ethanol (3.6.1), containing water (40 ml.). The stirred mixture is heated to near boiling and then cooled to 25° during 4 hours. The colorless crystalline material is collected, washed with cold 95% ethanol (500 ml.) and dried to give the tartrate salt of the (+)-enantiomer. Recrystallization from acetonitrile gives the purified tartrate salt.

C.   (+)-5-endo-Benzoyloxy-N-(3-dimethylaminopropyl)bicyclo[2.2.2]octane-2,3-di-endo-carboxylic Acid Imide Hydrochloride [(+)-(Ia)].

The (+)-enantiomer from step B is treated with an equivalent of ethanolic hydrogen chloride as described for the (—)enantiomer in I D. to give colorless crystals of the (+)-enantiomer HCl.

EXAMPLE 19

Preparation of 5-endo-(2-methyl-3-indolecarbonyloxy)-N-(3-dimethylaminopropyl)bicyclo[2.2.2]octane-2,3-di-endo-carboxylic acid imide hydrochloride [(+)-Ie].

Substitution in the procedure of example 6 for the indole-3-carboxylic acid used therein of an equimolar quantity of 2-methylindole-3-carboxylic acid produces the title product (+)-Ie.

EXAMPLE 20

Preparation of 5-endo-(2-bromo-3-indolecarbonyloxy)-N-(3-dimethylaminopropyl)bicyclo[2.2.2]octane-2,3-di-endo-carboxylic acid imide hydrochloride [(+)-If].

Substitution in the procedure of example 6 for the indole-3-carbonylic acid used therein of an equimolar quantity of 2-bromoindole-3-carboxylic acid produces the title product (+)-If.

EXAMPLE 21

Preparation of 5-endo-(3-indolecarbonyloxy)-N-(3-morpholinopropyl)bicyclo[2.2.2]octane-2,3-di-endo-carboxylic acid Imdie [(+)-Ig].

Substitution in the procedure of example 11 for the dicarboxylic acid imide III used therein of an equimolar quantity of IIIg produces the title product (+)-Ig.

EXAMPLE 22

Preparation of 5-endo-(3-indolecarbonyloxy)-N-(2-dimethylaminoethyl)bicyclo[2.2.2]octane-2,3-di-endo-carboxylic Acid Imide [(+)-(Ih)].

Substitution in the procedure of example 11 for the dicarboxylic acid imide used therein of an equimolar quantity of IIIb produces the title compound [(+)-(Ih)].

EXAMPLE 23

Preparation of 5-endo-(3-indolecarbonyloxy)-N-(3-piperidinopropyl)bicyclo[2.2.2]octane-2,3-di-endo-carboxylic Acid Imide (Ii).

Substitution in the procedure of example 11 for the dicarboxylic acid imide III used therein of an equimolar quantity of IIIe produces the title compound.

EXAMPLE 24

Preparation of 5-endo-(3-indolecarbonyloxy)-N-(3-methylaminopropyl)-bicyclo[2.2.2]octane-2,3-di-endo-carboxylic Acid Imide Hydrochloride (Ij).

A.   5-endo-(3-indolecarbonyloxy)-N-[3-2,2,2-trichloroethoxycarbonyl)-3-methylaminopropyl]-bicyclo[2.2.2]octane-2,3-di-endo-carboxylic Acid Imide.

Under anhydrous conditions, there is added 4.66 g. (22 mmoles) of trichloroethyl chloroformate to a mixture of 3.7 g. (10 mmoles) of compound (+)-Id and 2.0 g. (14.5 mmoles) potassium carbonate in 50 ml. benzene. The reaction mixture is refluxed for 18 hours. After cooling, ethyl acetate is added and the solution is filtered from the insolubles. The filtrate is washed with water, 5% $K_2CO_3$, water, 5% HCl, water and brine. After drying ($Na_2SO_4$) and filtration, the solvents are evaporated. In this manner, there is obtained a crude product which is the title product.

B.   5-endo-(3-indolecarbonyloxy)-N-(3-methylaminopropyl)bicyclo[2.2.2]octane-2,3-di-endo-carboxylic Acid Imide Hydrochloride.

Zinc dust (11.0 grams) is added to a solution of 5.56 g (10.5 mmoles) of the compound prepared in A above in 120 ml. of 90% acetic acid. The resulting reaction mixture is stirred at room temperature for 4 hours. The mixture is filtered and the filtrate evaporated to dryness. The residue is made basic by the addition of sodium bicarbonate and again is evaporated to dryness. Benzene (500 ml.) and $Na_2SO_4$ is added to the residue. The mixture is filtered; the filtrate is evaporated and the residue is dissolved in methanol. Some ether is added, and the hydrochloride salt is prepared with anhydrous hydrogen chloride gas. The precipitated salt is collected and after several recrystallizations from methanol-ether, there is obtained the title compound (Ij).

EXAMPLE 25

Preparation of 5-endo-(3-indolecarbonyloxy)-N-(3-aminopropyl)-bicyclo[2.2.2]octane-2,3-di-endo-carboxylic acid imide (Ik).

A. 5-endo-Hydroxy-bicyclo[2.2.2]octane-endo-2[N-(2-cyanoethyl)]carboxamide-endo-3-carboxylic acid γ-lactone (XX).

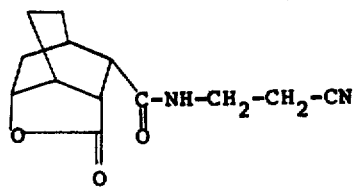

XX

A mixture of lactone-acid II (18.2 g; 0.1 mole), 150 ml. $SOCl_2$ and 250 ml $CH_2Cl$ containing 4 drops of DMF (dimethylformamide) is refluxed (60° C.) for 3 hours. After evaporating to dryness, benzene is added and removed under reduced pressure. After dissolving the acid chloride in 350 ml. $CH_2Cl_2$, there is added dropwise with vigorous stirring a solution of 3-aminopropionitrile (15.3 g; 0.21 mole) in 150 ml $CH_2Cl_2$. The resulting reaction mixture is refluxed for 2 hours. After cooling and filtering the insoluble materials, the filtrate is evaporated to dryness. The residue, so obtained, is slurried with a small amount of Ch₃CN to which ether is carefully added to produce the crystalline product.

B. 5-endo-(3-indolecarbonyloxy)-N-(2-cyanoethyl)-bicyclo[2.2.2]octane-endo-2,3-dicarboxylic acid imide (XIa).

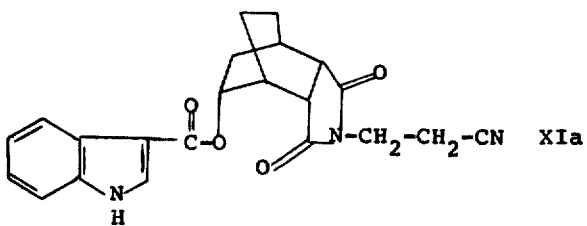

To a solution of lactone-amide XX (16 g; 0.068 mole) in 200 ml pyridine is added slowly the indole-3-carbonyl chloride (14.4 g; 0.08 mole). The resulting reaction mixture is heated at 110° C. for four hours. After evaporation to dryness, 5% K₂CO₃ is added and the mixture is extracted with ethyl acetate. The extracts are washed with brine, dried over Na₂SO₄, filtered and evaporated to dryness. Addition of ethanol and petroleum ether to the residue affords solid product XIa.

C. 5-endo-(3-indolecarbonyloxy)-N-(3-aminopropyl)-bicyclo[2.2.2]octane-endo-2,3-dicarboxylic acid imide hydrochloride (Ik).

A mixture of imide-nitrile XI (1.0 g; 2.96 mmole), 200 mg 10% Pd on carbon, 5 ml 5N HCl, and 95 ml ethanol is shaken under hydrogen at room temperature for 19 hours. After this time, water is added to the reaction mixture until all the solids dissolve. The catalyst is removed and the filtrate is evaporated to dryness, thereby affording the product Ik.

EXAMPLE 26

Preparation of
5-endo-(1-methylindolecarbonyloxy)-N-(3-dimethylaminopropyl)bicyclo[2.2.2]octane-2,3-di-endo-carboxylic acid imide [(+)-Iv].

Substitution in the procedure of example 11 for the 3-indolecarbonyl chloride used therein of an equimolar quantity of 1-methylindole-3-carbonyl chloride produces the title product (+)-Iv.

EXAMPLE 27

Preparation of
5-endo-(4-methyl-3-indolecarbonyloxy)-N-(3-dimethylaminopropyl)bicyclo[2.2.2]octane-2,3-di-endo-carboxylic acid imide [(+)-Iw].

Substitution in the procedure of example 11 for the 3-indolecarbonyl chloride used therein of an equimolar quantity of 4-methyl-3-indolecarbonyl chloride produces compound (+)-Iw.

EXAMPLE 28

Preparation of
5-endo-(4-methoxy-3-indolecarbonyloxy)-N-(3-dimethylaminopropyl)bicyclo[2.2.2]octane-2,3-di-endo-carboxylic acid imide [(+)-Ix].

Substitution in the procedure of example 11 for the 3-indolecarbonyl chloride used therein of an equimolar quantity of 4-methoxy-3-indolecarbonyl chloride produces the compound (+)-Ix.

EXAMPLE 29

Preparation of 5-endo-(4-trifluoromethyl-3-indolecarbonyloxy)-N-(3-dimethylaminopropyl)bicyclo[2.2.2]-octane-2,3-di-endo-carboxylic acid imide [(+)-Iy].

Substitution in the procedure of example 6 for the 3-indolecarboxylic acid used therein of an equimolar quantity of 4-trifluoromethyl-3-indolecarbonyloxy produces compound (+)-Iy.

EXAMPLE 30

Preparation of
5-endo-(5-hydroxy-3-indolecarbonyloxy)-N-(3-dimethylaminopropyl)bicyclo[2.2.2]octane-2,3-di-endo-carboxylic acid imide [(+)-Iq].

Substitution in the procedure of example 6 for the 3-indolecarbonyl chloride used therein of an equimolar quantity of 5-hydroxy-3-indolecarbonyl chloride produces compound (+)-Iq.

EXAMPLE 31

Preparation of
5-endo-(5-methoxy-3-indolecarbonyloxy)-N-(3-dimethylaminopropyl)bicyclo[2.2.2]octane-2,3-di-endo-carboxylic acid imide [(+)-Ir].

Substitution in the procedure of example 6 for the 3-indolecarbonyl chloride used therein of an equimolar quantity of 5-methoxy-3-indolecarbonyl chloride produces compound (+)-Ir.

EXAMPLE 32

Preparation of
5-endo-(5-methyl-3-indolecarbonyloxy)-N-(3-dimethylaminopropyl)bicyclo[2.2.2]octane-2,3-di-endo-carboxylic acid imide [(+)-Is].

Substitution in the procedure of example 6 for the 3-indolecarbonyl chloride used therein of an equimolar quantity of 5-methyl-3-indolecarbonyl chloride produces the compound (+)-Is.

EXAMPLE 33

Preparation of
5-endo-(2,3-dimethyl-3-indolecarbonyloxy)-N-(3-dimethylaminopropyl)bicyclo[2.2.2]octane-2,3-di-endo-carboxylic acid imide [(+)-It].

Substitution in the procedure of example 6 for the 3-indolecarbonyl chloride used therein of an equimolar quantity of 2,4-dimethyl-3-indolecarbonyl chloride produces the compound (+)-It.

EXAMPLE 34

Preparation of
5-endo-(6-chloro-5-methoxy-2-methyl-3-indolecarbonyloxy)-N-(3-dimethylaminoproply)-bicyclo[2.2.2]octane-2,3-di-endo-carboxylic acid imide [(+)-Iu].

Substitution in the procedure of example 6 for the 3-indolecarbonyl chloride used therein of an equimolar quantity of 6-chloro-5-methoxy-2-methyl-3-indolecarbonyl chloride produces the title compound [(+)-Iu].

EXAMPLE 35

(+)-5-endo-(3-Indolecarbonyloxy)-N-(3-dimethylaminopropyl)bicyclo[2.2.2]octane-2,3-di-endo-carboxylic acid Imide, Hydrochloride [BL-4764A, (+)-Id].

A. (+)-5-endo-Hydroxy-N-(3-dimethylaminopropyl bicyclo[2.2.2]octane-2,3-di-endo-carboxylic acid Imide [(+)-IIIa].

(+)-5-Endo-benzoyloxy-N-(3-dimethylaminopropyl)-bicyclo[2.2.2]octane-2,3-di-endo-carboxylic acid amide hydrochloride (3.65 g. 0.0086 mole) [(+)-Id] is suspended in 18.8 ml of 1.0N NaOH and heated to reflux with stirring for 45 minutes in an oil bath at 120°–125°C. The solution was then cooled, filtered and evaporated under reduced pressure to yield a white solid. The solid was then triturated with three 80 ml aliquots of hot EtOAc. The aliquots were combined and evaporated to yield an oil which solidified upon cooling. The solid was then resuspended in 100 ml cyclohexane and 15 ml EtOAc and heated to a reflux. Filtration of the hot solution and cooling to 20° C. produces a crystalline solid determined to be (+)-IIIa.

B. (+)-5-endo-(3-Indolecarbonyloxy)-N-(3-dimethylaminopropyl)bicyclo[2.2.2]octane-2,3-di-endo-carboxylic acid imide, hydrochloride [(+)-Id].

To a stirred mixture of indole-3-carboxylic acid (2.6 g. 0.015 mole) in Et₂O (40 ml) is added 3.0 ml of thionyl chloride and 1 drop of anhydrous dimethyl formamide (DMF). After stirring at 23° for 3 hrs., the mixture is filtered and the filtrate is stripped off excess reagent and solvent to yield the crude acid chloride (2.6 g) as a dark semi solid syrup. The acid chloride is taken up in 40 ml of dry CH₂Cl₂, 5 drops of pyridine is then added, followed by the (+)-IIIa alcohol (2.0 g, 0.0075 mole). The mixture is stirred at reflux for 2 hours under anhydrous conditions and then stripped of solvents under reduced pressure. The dark residue is chromatographed through a column of basic alumina (100 g), the product being eluted with 45% CHCl₃/45% Et₂O-25% EtOH and treated with HCl gas. Solvent removal, recrystallization of the crude solid from EtOH, and drying at 78° over P₂O₅ under high vacuum yields the pure hydrochloride salt.

EXAMPLE 36

(−)-5-Endo-(3-Indolecarbonyloxy)-N-(3-dimethylaminopropyl)bicyclo[2.2.2]octane-2,3-di-endo-carboxylic acid imide, hydrochloride.

A. (−)-5-Endo-Hydroxy-N-(3-dimethylaminopropyl)-bicyclo[2.2.2]octane-2,3-di-endo-carboxylic acid imide [(−)-IIIb].

Substitution in the procedure of example 35A for the compound (+)-Ia used therein of an equimolar quantity of (−)-Ia produces compound (−)-IIIa.

B. (−)-5-Endo-(3-Indolecarbonyloxy)-N-(3-dimethylaminopropyl)bicyclo[2.2.2]octane-2,3-di-endo-carboxylic acid imide, hydrochloride.

Indole-3-carboxylic acid (2.6 g, 0.015 mole) is converted to the crude acid chloride as described above in 35b. Treatment with the (−)-IIIa alcohol (2.0 g; 0.0075 mole) in CH₂Cl₂/pyridine as described in Example 35 gives the crude product. Chromatography on a column of basic alumina (100 g) give the purified free base upon elution with 33% CHCl₃/12% Et₂O/55% MeOH. The fractions containing the product are stripped of solvent, and the residual crude oil is taken up in 75% Et₂O—25% EtOH and treated with HCl gas. Solvent removal gives the hydrochloride as a crude brown solid. Two recrystallizations from EtOH followed by trituration with hot EtOAc and drying at 78° over P₂O₅ under high vacuum gives the product.

ECAMPLE 37

Preparation of 5-endo-(2-ethoxy-1-naphthoyloxy)-N-(3-dimethylaminopropyl)bicyclo[2.2.2]octane-2,3-di-endo-carboxylic acid imide hydrochloride [(+0-Idd].

Substitution in the procedure of example 5 for the 1-naphthoic acid used therein of an equimolar quantity of 2-ethoxy-1-naphthoic acid produces the title product (+)-Idd.

EXAMPLE 38

Preparation of 5-endo-(2-methoxy-1-naphthoyloxy)-N-(3-dimethylaminopropyl)bicyclo[2.2.2]octane-2,3-di-endo-carboxylic acid imide hydrochloride [(+)-Iee].

Substitution in the procedure of example 5 for the 1-naphthoic acid used therein of an equimolar quantity of 2-methoxy-1-naphthoic acid produces the title product (+)-Iee.

EXAMPLE 39

Preparation of 5-endo-(1-naphthoyloxy)-N-(3-morpholinopropyl)-bicyclo[2.2.2]octane-2,3-di-endo-carboxylic acid Imide (+) (Igg).

Substitution in the procedure of example 7 for the dicarboxylic acid imide III used therein of an equimolar quantity of IIIg produces the title product (+)-Igg.

EXAMPLE 40

Preparation of 5-endo-(1-naphthoyloxy)-N-(2-dimethylaminoethyl)-bicyclo[2.2.2]octane-2,3-di-endo-carboxylic Acid Imide (+) (Ijj).

Substitution in the procedure of example 5 for the dicarboxylic acid imide used therein of an equimolar quantity of IIIb produces the title compound (+)-Ijj.

EXAMPLE 41

Preparation of 5-endo-(1-naphthoyloxy)-N-(3-piperidinopropyl)bicyclo[2.2.2]octane-2,3-diendo-carboxylic Acid Imide (Ikk).

Substitution in the procedure of example 7 for the dicarboxylic acid imide III used therein of an equimolar quantity of IIIe produced the title compound.

EXAMPLE 42

Preparation of 5-endo-(1-naphthoyloxy)-N-(3-methylaminopropyl)-bicyclo[2.2.2]octane-2,3-di-endo-carboxylic Acid Imide Hydrochloride (Imm).

A. 5-endo-(1-naphthoyloxy)-N-[3-(2,2,2-trichloroethoxycarbonyl)-3-methylaminopropyl]-bicyclo[2.2.2]octane-2,3-di-endo-carboxylic Acid Imide.

Under anhydrous conditions, there is added 4.66 g. (22 mmoles) of trichloroethyl chloroformate to a mixture of 3.7 g. (10 mmoles) of compound (+)-Ic and 2.0 g. (14.5 mmoles) potassium carbonate in 50 ml. benzene. The reaction mixture is refluxed for 18 hours. After cooling, ethyl acetate is added and the solution is filtered from the insolubles. The filtrate is washed with water, 5% $K_2CO_3$, water, 5% HCl, water and brine. After drying ($Na_2SO_4$) and filtration, the solvents are evaporated. In this manner, there is obtained a crude product which is the title product.

B. 5-endo-(1-naphthoyloxy)-N-(3-methylaminopropyl)bicyclo[2.2.2]octane-2,3-di-endo carboxylic Acid Imide Hydrochloride.

Zinc dust (11.0 grams) is added to a solution of 5.56 g (10.5 mmoles) of the compound prepared in A above in 120 ml. of 90% acetic acid. The resulting reaction mixture is stirred at room temperature for 4 hours. The mixture is filtered and the filtrate evaporated to dryness. The residue is made basic by the addition of sodium bicarbonate and again is evaporated to dryness. Benzene (500 ml.) and $Na_2SO_4$ is added to the residue. The mixture is filtered; the filtrate is evaporated and the residue is dissolved in methanol. Some ether is added, and the hydrochloride salt is prepared with anhydrous hydrogen chloride gas. The precipitated salt is collected and after several recrystallizations from methanol-ether, there is obtained the title compound Imm.

EXAMPLE 43

Preparation of
5-endo-(1-naphthoyloxy)-N-(3-aminopropyl)bicyclo[2.2.2]octane-2,3-di-endo-carboxylic acid imide (Ikk).

A. 5-endo-(1-naphthoyloxy)-N-(2-cyanoethyl)bicyclo[2.2.2]octane-endo-2,3-dicarboxylic acid imide (XIb).

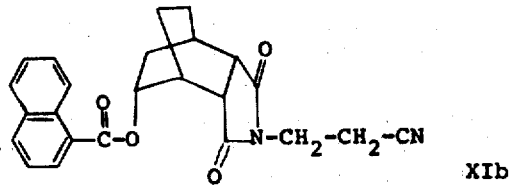

XIb

To a solution of lactone-amide XX (16 g; 0.068 mole) in 200 ml pyridine is added slowly the 1-naphthoic acid chloride (14.4 g; 0.102 mole). The resulting reaction mixture is heated at 110° C. for four hours. After evaporation to dryness, 5% $K_2CO_3$ is added and the mixture is extracted with ethyl acetate. The extracts are washed with brine, dried over $Na_2SO_4$, filtered and evaporated to dryness. Addition of ethanol and petroleum ether to the residue affords solid product XI.

B. 5-endo-(1-naphthoyloxy)-N-(3-aminopropyl)-bicyclo[2.2.2]octane-endo-2,3-dicarboxylic acid imide hydrochloride (Ikk).

A mixture of imide-nitrile XIb (1.0 g; 2.96 mmole), 200 mg 10% Pd on carbon, 5 ml 5N HCl, and 95 ml ethanol is shaken under hydrogen at room temperature for 19 hours. After this time, water is added to the reaction mixture until all the solids dissolve. The catalyst is removed and the filtrate is evaporated to dryness, thereby affording the product Ikk.

EXAMPLE 44

Preparation of
5-endo-(2-chloro-1-naphthoyloxy)-N-(3-dimethylaminopropyl)bicyclo[2.2.2]octane-2,3-di-endo-carboxylic acid imide [(+)-Ivv].

Substitution in the procedure of example 5 for the 1-naphthoic acid used therein of an equimolar quantity of 2-chloro-1-naphthoic acid produces the title product (+)-Ivv.

EXAMPLE 45

Preparation of
5-endo-(5-bromo-1-naphthoyloxy)-N-(3-dimethylaminopropyl)bicyclo[2.2.2]octane-2,3-di-endo-carboxylic acid imide [(+)-Iww).

Substitution in the procedure of example 5 for the 1-naphthoic acid used therein of an equimolar quantity of 5-bromo-1-naphthoic acid produces compound (+)-Iww.

EXAMPLE 46

Preparation of
5-endo-(2-hydroxy-1-naphthoyloxy)-N-(3-dimethylaminopropyl)bicyclo[2.2.2]octane-2,3-di-endo-carboxylic acid imide [(+)-Ixx].

Substitution in the procedure of example 5 for the 1-naphthoic acid used therein of an equimolar quantity of 2-hydroxy-1-naphthoic acid produces the compound (+)-Ixx.

EXAMPLE 47

Preparation of
5-endo-(8-methyl-1-naphthoyloxy)-N-(3-dimethylaminopropyl)bicyclo[2.2.2]octane-2,3-di-endo-carboxylic acid imide [(+)-Iyy].

Substitution in the procedure of example 5 for the 1-naphthoic acid used therein of an equimolar quantity of 8-methyl-1-naphthoic acid produces compound [(+)-Iyy].

EXAMPLE 48

Preparation of
5-endo-(2-ethyl-5-methoxy-1-naphthoyloxy)-N-(3-dimethylaminopropyl)bicyclo-[2.2.2]octane-2,3-di-endo-carboxylic acid imide [(+)-Iqq].

Substitution in the procedure of example 5 for the 1-naphthoic acid used therein of an equimolar quantity of 2-ethyl-5-methoxy-1-naphthoic acid produces compound (+)-Iqq.

EXAMPLE 49

Resolution of
(+)-5-endo-Naphthoyloxy-N-(3-dimethylaminopropyl)bicyclo[2.2.2]octane-di-endo-carboxylic acid imide [(+)-Ic].

A. (+)-5-endo-Naphthoyloxy-N-(3-dimethylaminopropyl)bicyclo[2.2.2]octane-2,3-di-endo-carboxylic acid imide [(+)-Ic].

A stirred mixture of the hydrochloride salt of Ic (4.2 g) in water (100 ml) and EtOAc (200 ml) is neutralized by the addition of sodium carbonate. The layers are separated and the aqueous layer reextracted with EtOAc (2×100 ml). The combined EtOAc extracts are washed with water, and dried (sodium sulfate). The removal of the EtOAc leaves a colorless oil which is crystallized from hot cyclohexane to yield the racemic base Ic.

B. (+)-10-Camphorsulfonic acid salt of (−)-5-endo-naphthoyloxy-N-(3-dimethylaminopropyl)bicyclo[2.2.2]octane-2,3-di-endo-carboxylic acid imide.

A hot solution of (+)-10 camphorsulfonic acid (1.16 g, 0.005 mole) in 90% ethanol (10 ml) is added to a hot solution of the racemic base Ic (2.1 g, 0.005 mole) in 90% ethanol (30 ml). The solution is gently warmed and diluted with 90% ethanol (125 ml). The solution is filtered and cooled slowly to room temperature (23°C) at which time a colorless crystalline material forms. The crystalline material is collected and washed with 90% ethanol (50 ml) to yield the title product. The mother liquor is cooled to 0°C. to yield a second crop of solid. Both crops are combined and the salt is recrystallized from methanol-water (10:1) to give colorless needles. The ethanolic mother liquor is saved for the isolation of the (+)-isomer.

C. (−)-5-endo-Naphthoyloxy-N-(3-dimethylaminopropyl)bicyclo[2.2.2]octane-2,3-di-endo-carboxylic acid imide [(−)-Ic].

The camphorsulfonic acid salt from B above was partitioned between a stirred mixture of EtOAc (100 ml) and water (100 ml) containing sodium carbonate (5 g). The aqueous layer is reextracted with EtOAc (100 ml). The combined EtOAc extracts are dried (Na$_2$SO$_4$) and removal of the EtOAc leaves an oil which is crystallized from hot cyclohexane to yield a colorless solid.

D. (−)-5-endo-Naphthoyloxy-N-(3-dimethylaminopropyl)bicyclo[2.2.2]octane-2,3-di-endo-carboxylic acid imide hydrochloride [(−)-Ic HCl].

The ethanolic mother liquor from the isolation of the levo isomer in B above is evaporated to dryness and the solid is partitioned between a stirred mixture of EtOAc (100 ml) and water (100 ml) containing sodium carbonate (5 g). The aqueous layer is reextracted with EtOAc (100 ml) and the combined EtOAc extracts are washed with water and dried (Na$_2$SO$_4$). The removal of the EtOAc leaves an oil which is redissolved in 30 ml of ethanol. Hydrogen chloride gas is bubbled into the solution of the (−)-isomer. The solution is cooled in ice to yield a colorless solid identified as the title product.

EXAMPLE 50

Preparation of 5-endo-3,4-5-Trimethoxybenzoyloxy-N-(3-dimethylaminopropyl)bicyclo[2.2.2]octane-2,3-di-endo-carboxylic Acid Imide Hydrochloride (Iaaa).

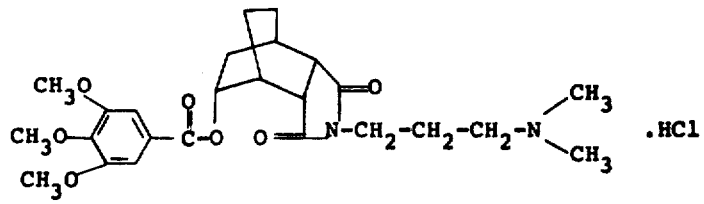

Substitution in the procedure of example 10 for the "appropriate" benzoyl halide used therein of an equimolar quantity of 3,4,5-trimethoxybenzoyl chloride and for the dicarboxylic acid imide III an equimolar quantity of IIIa produces the title compound which is collected as the hydrochloride salt.

EXAMPLE 51

Preparation of 5-endo-4-Nitrobenzoyloxy-N-(3-dimethylaminopropyl)bicyclo[2.2.2]octane-2,3-di-endo-carboxylic Acid Imide Hydrochloride (Ibbb).

Substitution in the procedure of example 10 for the "appropriate" benzoyl halide used therein of an equimolar quantity of 4-nitrobenzoyl chloride and for the dicarboxylic acid imide III an equimolar quantity of IIIa produces the title compound which is collected as the hydrochloride salt.

EXAMPLE 52

Preparation of 5-endo-4-Chlorobenzoyloxy-N-(3-dimethylaminopropyl)bicyclo[2.2.2]octane-2,3-di-endo-carboxylic Acid Imide Hydrochloride (IL).

Substitution in the procedure of example 10 for the "appropriate" benzoyl halide used therein of an equimolar quantity of 4-chlorobenzoyl chloride and for the dicarboxylic acid imide III an equimolar quantity of IIIa produces the title compound which is collected as the hydrochloride.

EXAMPLE 53

Preparation of 5-endo-3,4,5-trimethoxybenzoyl-N-(2-diethylaminoethyl)bicyclo[2.2.2]octane-2,3-di-endo-carboxylic Acid Imide Hydrochloride (Im).

Substitution in the procedure of example 10 for the "appropriate" benzoyl halide used therein of an equimolar amount of 3,4,5-trimethoxybenzoyl chloride and for the dicarboxylic acid imide III used therein of an equimolar quantity of IIIc produces the title product which is collected as the hydrochloride.

EXAMPLE 54

Preparation of 5-endo-4-Nitrobenzoyloxy-N-(3-morpholinopropyl)-bicyclo[2.2.2]octane-2,3-di-endo-carboxylic acid Imide (In).

Substitution in the procedure of example 10 for the "appropriate" benzoyl halide used therein of an equivalent amount of 4-nitrobenzoyl chloride and for the dicarboxylic acid imide III used therein an equivalent amount of 4-nitrobenzoyl chloride and for the dicarboxylic acid imide III used therein an equimolar quantity of IIIg produces the title product.

EXAMPLE 55

Preparation of 5-endo-4-Chlorobenzoyloxy-N-(3-morpholinopropyl)-bicyclo[2.2.2]octane-2,3-di-endo-carboxylic acid Imide Hydrochloride (Io).

Substitution in the procedure of example 10 for the "appropriate" benzoyl halide used therein of an equivalent amount of 4-chlorobenzoyl chloride and for the dicarboxylic acid imide III used therein an equimolar quantity of IIIg produces the title product which is collected as the hydrochloride.

EXAMPLE 56

Preparation of 5-endo-Benzoyloxy-N-(2-dimethylaminoethyl)bicyclo[2.2.2]octane-2,3-di-endo-carboxylic Acid Imide (Ip).

Substitution in the procedure of example 10 for the "appropriate" benzoyl halide used therein of an equimolar quantity of benzoyl chloride and for the dicarboxylic acid imide an equimolar quantity of IIIb produces the title compound.

EXAMPLE 57

Preparation of 5-endo-4-Nitrobenzoyloxy-N-(3-piperidinopropyl)-bicyclo[2.2.2]octane-2,3-di-endo-carboxylic Acid Imide (Iccc).

Substitution in the procedure of example 10 for the "appropriate" benzoyl halide used therein of an equimolar quantity of 4-nitrobenzoyl chloride and for the dicarboxylic acid imide III used therein of IIIe produces the title compound.

EXAMPLE 58

Preparation of 5-endo-Benzoyloxy-N-(2-dimethylaminoethyl)bicyclo[2.2.2]octane-2,3-di-endo-carboxylic Acid Imide (Iddd).

Substitution in the procedure of example 10 for the "appropriate" benzoyl halide used therein of an equimolar amount of benzoyl chloride and for the dicarboxylic acid amide III used therein an equimolar quantity of IIIb produces the title compound.

EXAMPLE 59

Preparation of 5-endo-3,4,5-Trimethoxybenzoyl-N-(2-dimethylaminoethyl)bicyclo[2.2.2]octane-2,3-di-endo-carboxylic Acid Imide (Ieee).

Substitution in the procedure of example 10 for the "appropriate" benzoyl halide used therein of an equimolar quantity of 3,4,5-trimethoxybenzoyl chloride and for the dicarboxylic acid imide III used therein an equimolar quantity of IIIb produces the title compound.

EXAMPLE 60

Preparation of 5-endo-Benzoyloxy-N-(3-methylaminopropyl)bicyclo[2.2.2]octane-2,3-di-endo-carboxylic Acid Imide Hydrochloride (Ifff).

A. 5-endo-Benzoyloxy-N-[3-(2,2,2-trichloroethoxycarbonyl)-3-methylaminopropyl]bicyclo[2.2.2]octane-2,3-di-endo-carboxylic Acid Imide.

Under anhydrous conditions there is added 4.66 g. (22 moles) of trichloroethyl chloroformate to a mixture of 3.7 g. (10 mmoles) of compound Ia and 2.0 g. (14.5 mmoles) potassium carbonate in 50 ml. benzene. The reaction mixture is refluxed for 18 hours. After cooling, ethyl acetate is added and the solution is filtered from the insolubles. The filtrate is washed with water, 5% $K_2CO_3$, water, 5% HCl, water and brine. After drying ($Na_2SO_4$) and filtration, the solvents are evaporated. In this manner, there is obtained a crude product which when recrystallized from ethyl acetate-skelly B (essentially n-hexane) afforded the pure title product.

B. 5-endo-benzoyloxy-N-(3-methylaminopropyl)-bicyclo[2.2.2]octane-2,3-di-endo-carboxylic Acid Imide Hydrochloride.

Zinc dust (11.0 grams) is added to a solution of 5.56 g. (10.5 mmoles) of the compound prepared in A above in 120 ml. of 90% acetic acid. The resulting reaction mixture is stirred at room temperature for four hours. The mixture is filtered and the filtrate evaporated to dryness. The residue is made basic by the addition of sodium bicarbonate and again is evaporated to dryness. Benzene (500 ml.) and $Na_2SO_4$ is added to the residue. The mixture is filtered; the filtrate is evaporated and the residue is dissolved in methanol. Some ether is added, and the hydrochloride salt was prepared with anhydrous hydrogen chloride gas. The precipitated salt is collected and after several recrystallizations from methanol-ether, there is obtained the title compound.

EXAMPLE 61

Preparation of 5-endo-Benzoyloxy-N-(3aminopropyl)bicyclo[2.2.2]octane-2,3-di-endo-carboxylic Acid Imide (Iggg).

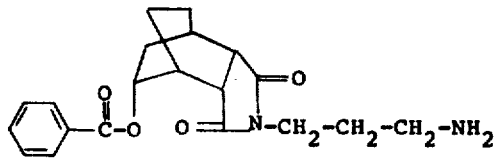

A. 5-endo-Benzoyloxy-N-(2-cyanoethyl)bicyclo[2.2.2]-octane-2,3-di-endo-carboxylic Acid Imide (XIc).

Substitution in the procedure of example 10 for rthe appropriate benzoyl halide and imide (III) used therein of equimolar quantities of benzoyl chloride and compound XX produces the title compound XIc.

B. 5-endo-Benzoyloxy-N-(3-aminopropyl)bicyclo[2.2.2]octane-2,3-di-endo-carboxylic Acid Imide.

One-tenth mole of compound XIc prepared in A above is dissolved in 200 ml. of ethanol and hydrogenated at 60 psi using Pd/C and hydrogen until two-tenths mole of hydrogen is absorbed to produce compound (Iggg).

EXAMPLE 62

General Procedure for the Separation of racemic 5-endo-benzoyloxy-N-[amino(lower)alkyl]bicyclo[2.2.2]octane-2,3-di-endo-carboxylic Acid Imides into its (+) and (−) Enantiomers.

1. Treatment of the racemic base with (+)-10-camphorsulfonic acid in ethanol-water gave the diastereoisomeric salt of the (−)-isomer. Decomposition of this salt with aqueous sodium carbonate afforded the (−)-enantiomer which was converted to the hydrochloride with ethanolic hydrogen chloride.

2. The mother liquor from the first step was concentrated to leave a mixture of diastereoisomeric salts. Neutralization of this mixture with aqueous sodium carbonate gave a mixture of the (+)- and (−)- isomers, which was greatly enriched in the (+)-enantiomer. In one small scale experiment it was possible to obtain substantially pure (+)-isomer by recrystallization from cyclohexane. In larger scale experiments, it was more expedient to purify the mixture through diastereoisomer formation with (−)-tartaric acid to give the salt of (−)-tartaric acid with the (+)-enantiomer, which is subsequently decomposed to produce the (+)-enantiomer.

EXAMPLE 63

Preparation of (±)-5-endo-N-(o-Chlorophenyl)carbamoyloxy-N-(3-dimethylaminopropyl)bicyclo[2.2.2]octane-2,3-di-endo-carboxylic acid imide, hydrochloride (Ihhh).

A mixture of 5-endo-hydroxy-N-(3-dimethylpropyl)-bicyclo[2.2.2]octane-2,3-di-endo-carboxylic acid imide (5.32 g, 0.02 mole) and o-chlorophenylisocyanate (15 ml) in 15 ml of dry pyridine is stirred at 25° C under anhydrous conditions for 18 hours. The reaction mixture is diluted with 100 ml Et$_2$O, precipitated a white solid, which is then crystalized from 100% EtOH.

EXAMPLE 64

Preparation of 5-endo-N-(p-chlorophenyl)carbamoyloxy-N-(3-morpholinopropyl)bicyclo[2.2.2]octane-2,3-di-endo-carboxylic acid Imide Hydrochloride (jjj).

Substitution in the procedure of example 4 or 8 for the "appropriate" isocyanate used therein of an equivalent amount of 4-chlorophenylisocyanate and for the dicarboxylic acid imide III used therein an equimolar quantity of IIIg produces the title product which is collected as the hydrochloride (using a method comparable to that employed in example 4).

EXAMPLE 65

Preparation of 5-endo-N-phenylcarbamoyloxy-N-(2-dimethylaminoethyl)bicyclo[2.2.2]octane-2,3-di-endo-carboxylic Acid Imide (Ikkk).

Substitution in the procedure of example 4 or 8 for the "appropriate" isocyanate used therein of an equimolar quantity of phenylisocyanate and for the dicarboxylic acid imide an equimolar quantity of IIIb produces the title compound.

EXAMPLE 66

Preparation of 5-endo-N-(p-nitrophenyl)carbamoyloxy-N-(3-piperidonopropyl)bicyclo[2.2.2]octane-2,3-di-endo-carboxylic Acid Imide (Immm).

Substitution in the procedure of example 4 or 8 for the "appropriate" isocyanate used therein of an equimolar quantity of p-nitrophenylisocyanate and for the dicarboxylic acid imide III used therein of IIIe produces the title compound.

EXAMPLE 67

Preparation of 5-endo-N-phenylcarbamoyloxy-N-(2-dimethyl-aminoethyl)bicyclo[2.2.2]octane-2,3-di-endo-carboxylic ACid Imide (Innn).

Substitution in the procedure of example 4 or 8 for the "appropriate" isocyanate used therein of an equimolar amount of phenylisocyanate and for the dicarboxylic acid imide III used therein an equimolar quantity of IIIb produces the title compound.

EXAMPLE 68

Preparation of 5-endo-N-phenylcarbamoyloxy-N-(3-methylaminopropyl)bicyclo[2.2.2]octane-2,3-di-endo-carboxylic Acid Imide Hydrochloride (Iooo).

A. 5-endo-N-phenylcarbamoyloxy-N-[3-(2,2,2-trichloroethoxy-carbonyl)-3-methylaminopropyl]-bicyclo[2.2.2]octane-2,3-di-endo-carboxylic Acid Imide.

Under anhydrous conditions there is added 22 mmoles of trichloroethyl chloroformate to a mixture of 10 mmoles of compound Ib and 2.0 g. (14.5 mmoles) potassium carbonate in 50 ml. benzene. The reaction mixture is refluxed for 18 hours. After cooling, ethyl acetate is added and the solution is filtered from the insolubles. The filtrate is washed with water, 5% K$_2$CO$_3$, water, 5% HCl, water and brine. After drying (Na$_2$SO$_4$) and filtration, the solvents are evaporated. In this manner, there is obtained a crude product which when recrystallized from ethyl acetate-skelly B (essentially n-hexane) affords title product.

B. 5-endo-N-phenylcarbamoyloxy-N-(3-methylaminopropyl)bicyclo[2.2.2]octane-2,3-di-endo-carboxylic Acid Imide Hydrochloride.

Zinc dust (11.0 grams) is added to a solution of 5.56 g. (10.5 mmoles) of the compound prepared in A above in 120 ml. of 90% acetic acid. The resulting reaction mixture is stirred at room temperature for four hours. The mixture is filtered and the filtrate evaporated to dryness. The residue is made basic by the addition of sodium bicarbonate and again is evaporated to dryness. Benzene (500 ml.) and Na$_2$SO$_4$ is added to the residue. The mixture is filtered; the filtrate is evaporated and the residue is dissolved in methanol. Some ether is added, and the hydrochloride salt is prepared with anhydrous hydrogen chloride gas. The precipitated salt is collected and after several recrystallizations from methanol-ether, there is obtained the title compound (Ij).

EXAMPLE 70

Preparation of 5-endo-N-phenylcarbamoyloxy-N-(3-aminopropyl)-bicyclo[2.2.2]octane-2,3-di-endo-carboxylic acid imide (Ippp).

A).

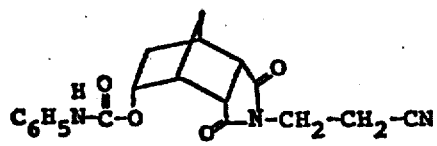

XId

To a solution of lactone-amide XX (16 g; 0.068 mole) in 200 ml pyridine is added slowly the phenylisocyanate (0.102 mole). The resulting reaction mixture is heated to 110°C. for 4 hours. After evaporation to dryness, 5% K₂CO₃ is added and the mixture is extracted with ethyl acetate. The extracts are washed with brine, dried over Na₂SO₄, filtered and evaporated to dryness. Addition of ethanol and petroleum ether to the residue affords the product.

B. 5-endo-N-phenylcarbamoyloxy-N-(3-aminopropyl)bicyclo[2.2.2]octane-endo-2,3-dicarboxylic acid imide hydrochloride.

A mixture of imide-nitrile XId (1.0 g; 2.96 mmole), 200 mg 10% Pd on carbon, 5 ml 5N HCl, and 95 ml ethanol are shaken under hydrogen at room temperature for 19 hours. After this time, water is added to the reaction mixture until all the solids dissolve. The catalyst is removed and the filtrate is evaporated to dryness, thereby affording the product.

We claim:
1. A compound having the formula

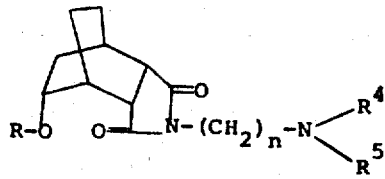

wherein R is a radical having the formula

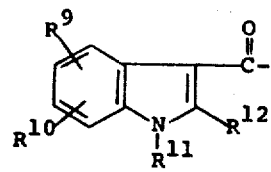

wherein $R^{11}$ is hydrogen or (lower)alkyl, $R^{12}$ is chloro, bromo, fluoro, hydrogen or (lower)alkyl and $R^9$ and $R^{10}$ are alike or different and each is H, Cl, Br, F, (lower)alkyl, nitro, CF₃, OH or (lower)alkoxy; n is an integer of 2 to 4 inclusive and $R^4$ or $R^5$ are alike or different and each is H, (lower)alkyl or when taken together with the nitrogen a radical of the formula

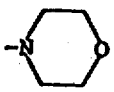, 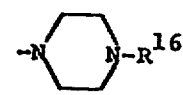,

 or 

in which $R^{16}$ is (lower)alkyl; or a pharmaceutically acceptable acid addition salt thereof.

2. A compound of claim 1 wherein R is a radical having the formula

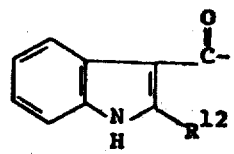

wherein $R^{12}$ is H, F, Cl, methoxy, ethoxy or n-propoxy.

3. A compound having the formula

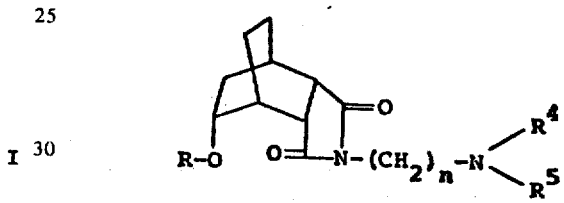

wherein R is a radical having the formula

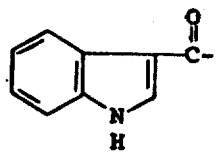, n is an integer of 2 to 4 inclusive and
$R^4$ and $R^5$ are alike or different and each is (lower)alkyl; or a pharmaceutically acceptable acid addition salt thereof.

4. The compound of claim 1 wherein $R^4$ and $R^5$ are methyl and R is 3-indolecarbonyl; or the hydrochloride salt thereof.

5. The essentially pure levorotatory isomers of the compounds of claim 1.

6. The essentially pure dextrorotatory isomers of the compounds of claim 1.

* * * * *